(12) United States Patent
Serra De Mattos et al.

(10) Patent No.: US 11,752,305 B2
(45) Date of Patent: Sep. 12, 2023

(54) HAND-HELD DEVICE FOR INSERTING A NEEDLE INTO A NON-HOMOGENEOUS MATERIAL

(71) Applicant: FONDAZIONE ISTITUTO ITALIANO DI TECNOLOGIA, Genoa (IT)

(72) Inventors: Leonardo Serra De Mattos, Genoa (IT); Zhuoqi Cheng, Genoa (IT); Brian L. Davies, London (GB); Darwin Gordon Caldwell, Serra Ricco (IT)

(73) Assignee: FONDAZIONE ISTITUTO ITALIANO DI TECNOLOGIA, Genoa (IT)

( * ) Notice: Subject to any disclaimer, the term of this patent is extended or adjusted under 35 U.S.C. 154(b) by 162 days.

(21) Appl. No.: 16/617,055

(22) PCT Filed: May 28, 2018

(86) PCT No.: PCT/EP2018/063871
§ 371 (c)(1),
(2) Date: Nov. 26, 2019

(87) PCT Pub. No.: WO2018/219842
PCT Pub. Date: Dec. 6, 2018

(65) Prior Publication Data
US 2020/0139086 A1    May 7, 2020

(30) Foreign Application Priority Data

May 31, 2017    (IT) ..................... 102017000059659

(51) Int. Cl.
*A61M 25/06*     (2006.01)
*A61B 5/15*      (2006.01)
*A61B 5/153*     (2006.01)

(52) U.S. Cl.
CPC ..... *A61M 25/0606* (2013.01); *A61B 5/15003* (2013.01); *A61B 5/1535* (2013.01);
(Continued)

(58) Field of Classification Search
CPC ........ A61M 25/0606; A61M 2205/332; A61M 2205/3375; A61M 2205/8206;
(Continued)

(56) References Cited

U.S. PATENT DOCUMENTS

| 5,411,486 A | * | 5/1995 | Zadini | ................. A61M 5/3269 |
| | | | | 128/919 |
| 2002/0042594 A1 | * | 4/2002 | Lum | ...................... A61B 18/14 |
| | | | | 604/117 |
| 2005/0148940 A1 | * | 7/2005 | Miller | .............. A61B 17/32002 |
| | | | | 604/187 |

FOREIGN PATENT DOCUMENTS

| EP | 0730880 B1 | 9/1996 |
| WO | 9305832 A1 | 4/1993 |
| WO | 2016207729 A2 | 12/2016 |

OTHER PUBLICATIONS

International Search Report for International Patent Application No. PCT/EP2018/063871, dated Aug. 23, 2018, 5 pages.

(Continued)

*Primary Examiner* — Lauren P Farrar
*Assistant Examiner* — Hamza A Darb
(74) *Attorney, Agent, or Firm* — Armstrong Teasdale LLP

(57) ABSTRACT

A hand-held device is provided for precisely positioning a needle tip at a desired target position into a non-homogeneous material, including a blood vessel. The hand-held device includes a casing hand-held by an operator, a shaft extending along a longitudinal axis and carrying the needle, the shaft mounted in the casing and coupled to the casing to move as a single piece therewith along the longitudinal axis. The hand-held device further includes a sensor unit to (Continued)

provide signals indicative of a physical characteristic of the material wherein the needle tip has to be inserted, and a control unit configured to determine, based on the signals received from the sensor unit, whether the needle tip has reached the target position and to operate a decoupling unit to decouple the shaft and the needle from the casing or to operate an actuating unit to actively move the shaft relative to the casing.

10 Claims, 6 Drawing Sheets

(52) U.S. Cl.
CPC .. *A61B 5/150748* (2013.01); *A61B 5/150992* (2013.01); *A61M 2205/332* (2013.01); *A61M 2205/3375* (2013.01); *A61M 2205/8206* (2013.01)

(58) Field of Classification Search
CPC .. A61M 2005/1585; A61M 2205/3327; A61M 5/16836; A61M 25/01; A61M 5/46; A61B 5/15003; A61B 5/150748; A61B 5/150992; A61B 5/1535
See application file for complete search history.

(56) References Cited

OTHER PUBLICATIONS

Written Opinion for International Patent Application No. PCT/EP2018/063871, dated Aug. 23, 2018, 5 pages.

* cited by examiner

HAND-HELD DEVICE FOR INSERTING A NEEDLE INTO A NON-HOMOGENEOUS MATERIAL

CROSS-REFERENCE TO RELATED APPLICATIONS

This application is a National Phase filing of PCT International Application No. PCT/EP2018/063871, having an International Filing Date of May 28, 2018, claiming priority to Italian Patent Application No. 102017000059659, having a filing date of May 31, 2017 each of which is hereby incorporated by reference in its entirety.

FIELD OF THE INVENTION

The present invention relates to a hand-held device for inserting a needle into a non-homogeneous material, particularly for intravenous catheterization.

BACKGROUND OF THE INVENTION

EP 0 730 880 A discloses a manual catheterization device provided with an actuated needle retraction mechanism. This known device aims at improving the catheterization process as it helps the medical technician to properly dispose of the needle to avoid a needlestick with a contaminated needle. The device includes a generally hollow barrel that houses a needle hub. A needle is affixed to the distal end of the needle hub and is aligned to extend through an opening in the distal end of the barrel. The needle extends through a catheter hub and a catheter affixed to the catheter hub. The device further includes a spring that is disposed in the barrel lumen to cooperate with the needle hub to urge the latter toward the proximal end of the barrel. A latch actuator is releasably engaged with the catheter hub. A latch which cooperates with the latch actuator is movable between a first position in which it maintains the needle hub adjacent to the distal end of the barrel and a second position allowing the spring to urge the needle hub to the proximal end of the barrel. Due to the vibrations inducted by the activation of the spring the operator may experience discomfort during the needle insertion process or during the needle extraction process after the puncture. Moreover, such a known device has no capability to guide insertion of the needle into the material.

SUMMARY OF THE INVENTION

It is therefore an object of the present invention to provide a hand-held device for precisely positioning a needle tip in a non-homogeneous material, particularly for intravenous catheterization, which is safer and more comfortable to use than the prior art discussed above.

This and other objects are fully achieved according to the present invention by a hand-held device having the features described and claimed herein.

In short, the invention is based on the idea of providing a hand-held device comprising a decoupling unit or an actuating unit operatively arranged between the needle and the casing for decoupling the needle from the casing, so that the needle does not move as a single piece with the casing along its longitudinal axis, or for moving the needle in a controlled manner along its longitudinal axis in the opposite direction relative to the casing during the insertion process, respectively, a sensor unit configured to detect a condition where the needle tip has reached a target position in the non-homogeneous material and a control unit operatively connected to said decoupling unit or said actuating unit and said sensor unit and configured to operate said decoupling unit or said actuating unit upon detection by said sensor unit that the needle tip has reached the target position.

By virtue of such a configuration, the hand-held device of the invention allows to introduce the needle within the target non-homogeneous material stopping the needle tip in the correct position or retracting it even though the operator moves the casing of the device forwards into the material. This is especially helpful when performing intravenous catheterization, in particular on difficult patients, comprising paediatric, elderly or diabetic patients. Moreover, with the use of such a device less training is required from the operator to achieve good injection results.

Further features and advantages of the present invention will become apparent from the following detailed description, given purely by way of non-limiting examples with reference to the drawings.

DETAILED DESCRIPTION

The present invention will be described hereafter with specific reference to its application to the catheterization process, i.e. the insertion of a catheter within a blood vessel. This specific application is however to be construed as not limiting the scope of the invention, since the invention may be used in many other applications, comprising tissue biopsy (e.g. from a brain, liver, etc.), brachytherapy, i.e. the insertion of radioactive seeds inside that the patient for cancer treatment, blood sampling, i.e. the insertion of a needle within a blood vessel, or spinal cord puncture.

Figure 1:
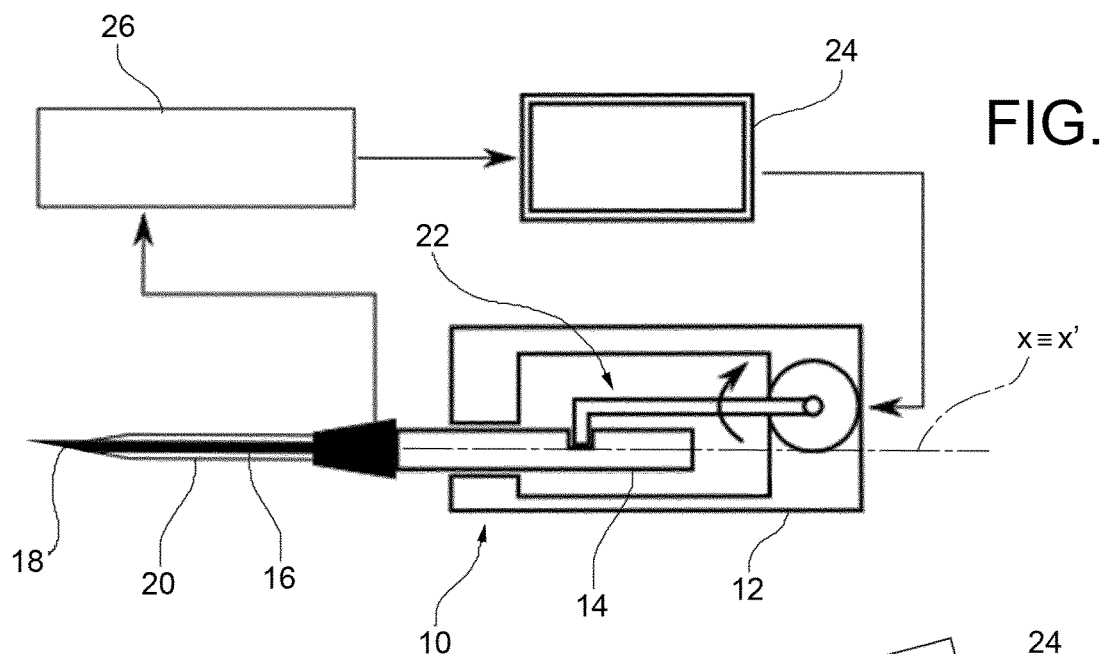
FIG. 1 schematically shows a hand-held device for inserting a needle into a non-homogeneous material according to the present invention.

FIG. 1 shows a very schematic representation of a hand-held catheterization device according to the present invention (hereinafter simply referred to as "the device"), where the device is generally indicated 10.

With reference to FIG. 1, the device 10 basically comprises a main body or casing 12 (hereinafter referred to simply as casing), which is suitably sized to be held by the operator's hand, and a shaft 14, which is partially received within the casing 12 and carries at its distal end a needle 16 having a tip 18 and a catheter 20 disposed around the needle 16. The longitudinal axis of the shaft 14 is indicated x, while the longitudinal axis of the needle 16 is indicated x'. The longitudinal axes x and x' are parallel to each other and may also coincide with each other (as in the example illustrated in FIG. 1).

The shaft 14 is normally coupled to the casing 12, so that it is moved by the operator as a single piece with the casing 12. The shaft 14 can however be decoupled from the casing 12, once the needle tip 18 has reached a target position, for example a blood vessel, by a unit 22 (acting in this case as a decoupling unit), so that it is no more coupled to the casing 12 and is therefore free to move relative to the casing 12 along the direction of its longitudinal axis x. Once the shaft 14, and therefore also the needle 16 carried by it, is decoupled from the casing 12, a possible further forward movement of the casing 12 caused by the operator is no longer transmitted to the needle 16, and therefore the needle tip 18 remains at the target position irrespective of possible movements of the casing 12 caused (either intentionally or unintentionally) by the operator.

The device 10 further comprises a control unit 24 (for example a microcontroller) configured to control the decoupling unit 22 to decouple the shaft 14, and therefore also the needle 16 and the catheter 20 carried by the shaft 14, from the casing 12 when the needle tip 18 has reached the target position (that is to say, in case of a catheterization device, a blood vessel).

In order for the control unit 24 to be informed about the needle tip 18 reaching the target position, the device 10 further comprises a sensor unit 26 arranged to measure a physical characteristic of the material at the needle tip 18, including an electrical impedance, a pressure, a colour, a temperature, etc., or to measure a vibration, a sound, a force change, etc., and to send corresponding signals to the control unit 24. Based on the signals received by the sensor unit 26, the control unit 24 is able to discriminate between different materials at the needle tip 18 to determine whether the needle tip 18 has reached the target position. In case, for example, of a sensor unit 26 made as an impedance sensing circuit and of a target position constituted by a blood vessel, the control unit 24 will analyze the impedance signals provided by the sensor unit 26 and determine whether they are within the range of blood. In the affirmative, the control unit 24 will command the decoupling unit 22 to decouple the shaft 14, and therefore also the needle 16, from the casing 12.

The device 10 is preferably battery-operated by an embedded rechargeable or replaceable battery back (not shown). Alternatively, the device 10 may be powered by an external DC adapter.

Figure 2A:
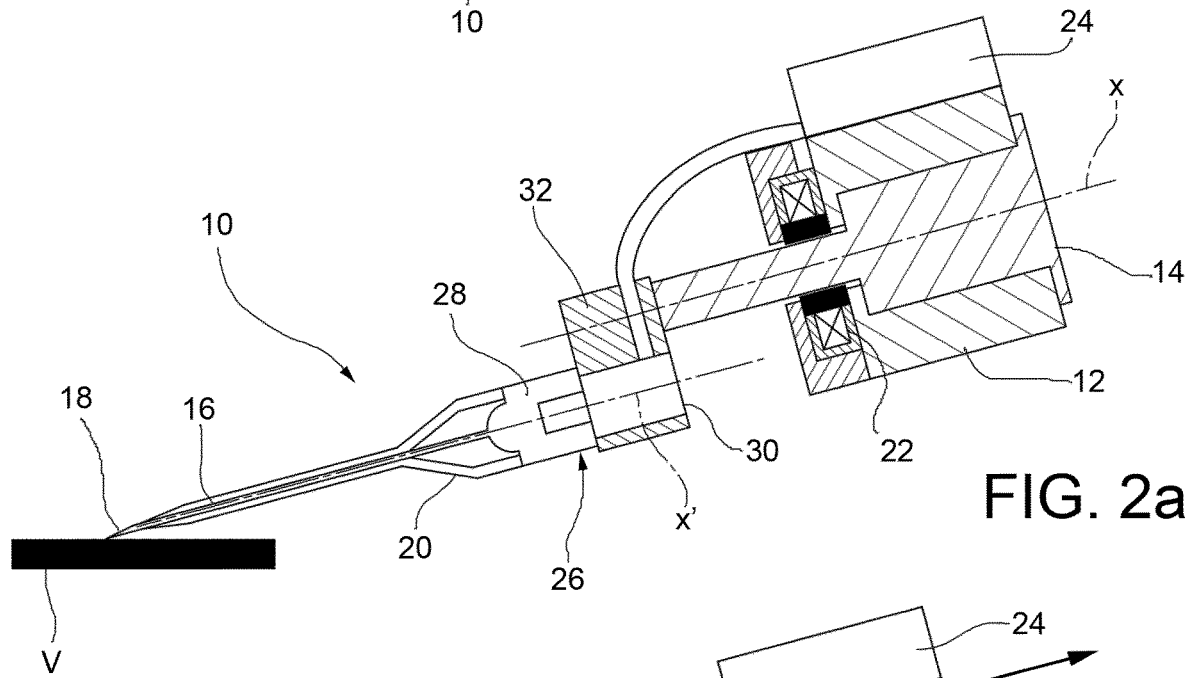
FIGS. 2a and 2b are schematic views showing a first embodiment of a device according to the invention, in a first operating condition where the needle is coupled to the casing of the device and in a second operating condition where the needle is decoupled from the casing, respectively.
Figure 2B:
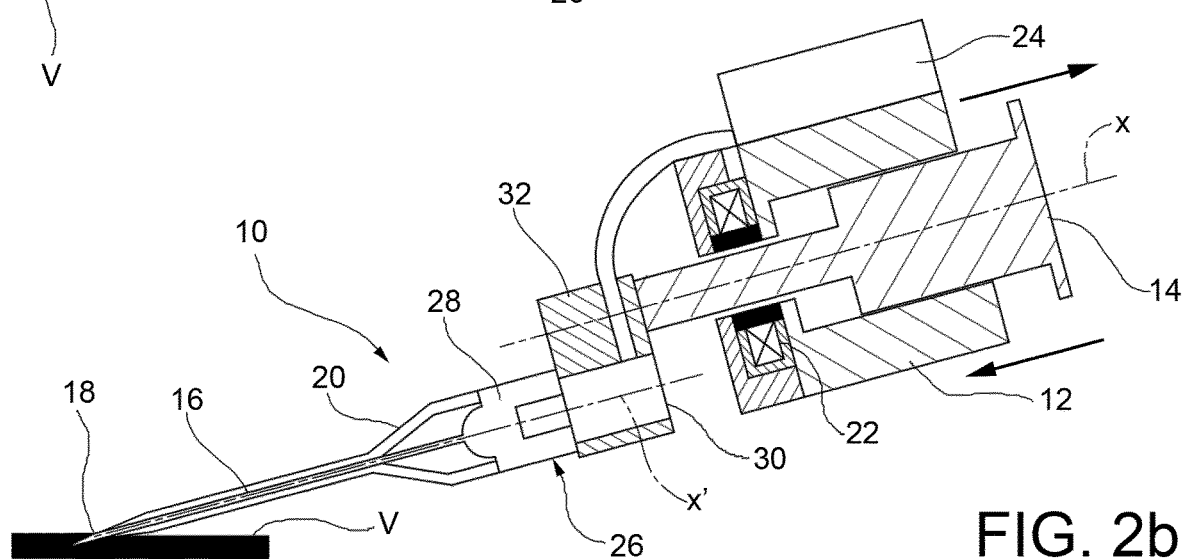

With reference now to FIGS. 2a and 2b, a first embodiment of the invention is shown, where the device 10 is configured to insert a catheter 20 into a vein V. FIG. 2a shows the device 10 before the needle 16 has punctured the vein V, while FIG. 2b shows the device 10 once the needle 16 has punctured the vein V and the needle tip 18 is therefore within the vein V.

According to this embodiment, the decoupling unit 22 comprises an electrical clutch that is normally engaged and clamps therefore the shaft 14, so that the shaft 14 is normally coupled to the casing 12 (FIG. 2a). When activated, the electrical clutch unclamps the shaft 14, thereby allowing the shaft 14, and hence the needle 16 and the catheter 20 with it, to freely move along its longitudinal axis x relative to the casing 12 at least in one direction (FIG. 2b), so that if the operator moves the casing 12 further towards the vein V, the shaft 14 may retract inside the casing 12 thereby allowing the needle tip 18 to remain in the target position in the vein V.

As far as the sensor unit 26 is concerned, it includes an impedance sensor contained in a concentric electrode needle 28 to measure the electrical impedance between the needle tip 18 and the needle shaft. The concentric electrode needle 28 is plugged onto a connector element 30 which is in turn mounted onto the distal end of the shaft 14 through a connecting member 32, so that the concentric electrode needle 28 is drivingly connected to the shaft 14. The sensed electrical impedance signal is transferred from the sensor unit 26 to the control unit 24, in order for the latter to be able to determine whether the needle tip 18 has reached a vein and, if so, to activate the electrical clutch to decouple the shaft 14 from the casing 12.

Figure 3:
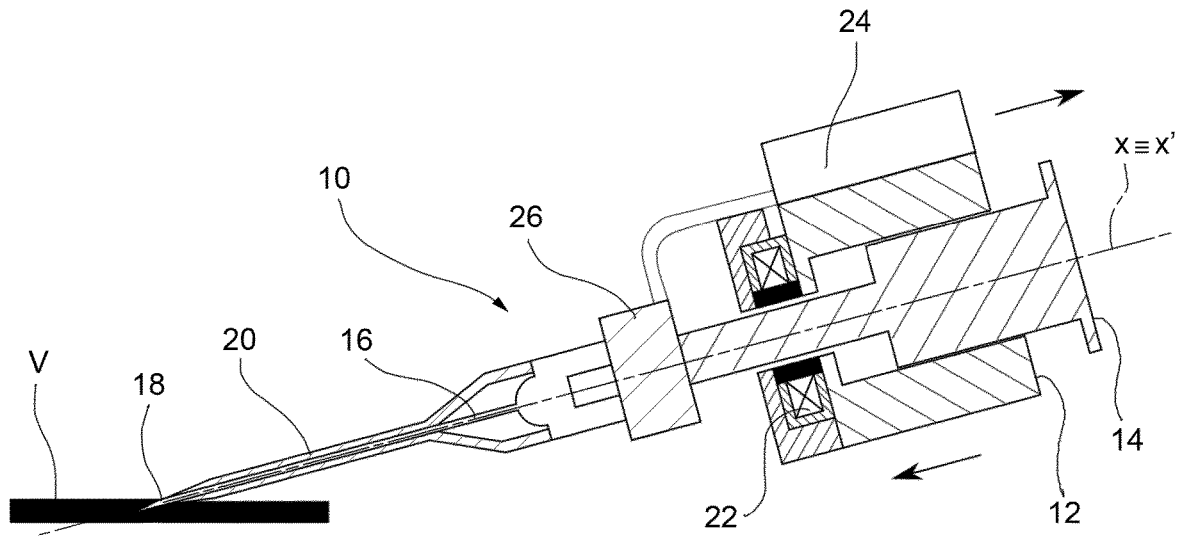
FIG. 3 is a schematic view showing a second embodiment of a device according to the invention, in the above-mentioned second operating condition.

FIG. 3, where parts and elements identical or corresponding to those of FIGS. 2a and 2b are designated with the same reference numerals, shows a second embodiment of the invention which differs from the first embodiment of FIGS. 2a and 2b in that the sensor unit 26 is arranged to detect the acoustic or near-acoustic signal generated by the puncture of the vein, i.e. the so-called "pop" sound described by practitioners or the needle vibration.

In this case, the sensor unit 26 comprises a microphone for acquiring and using the acoustic signals and an appropriate signal processing system configurator to distinguish the sound generated when penetrating the vein from other noises generated when penetrating adjacent tissues. The sensor unit 26 may also comprise filters configured to remove these other noises and thus improve the signal-to-noise ratio. Such an acoustic based detection system may be used as an alternative to the impedance-based detection system described above in connection with the first embodiment of FIGS. 2a and 2b or as a further detection system in addition to the above impedance-based detection system.

Figure 4A:
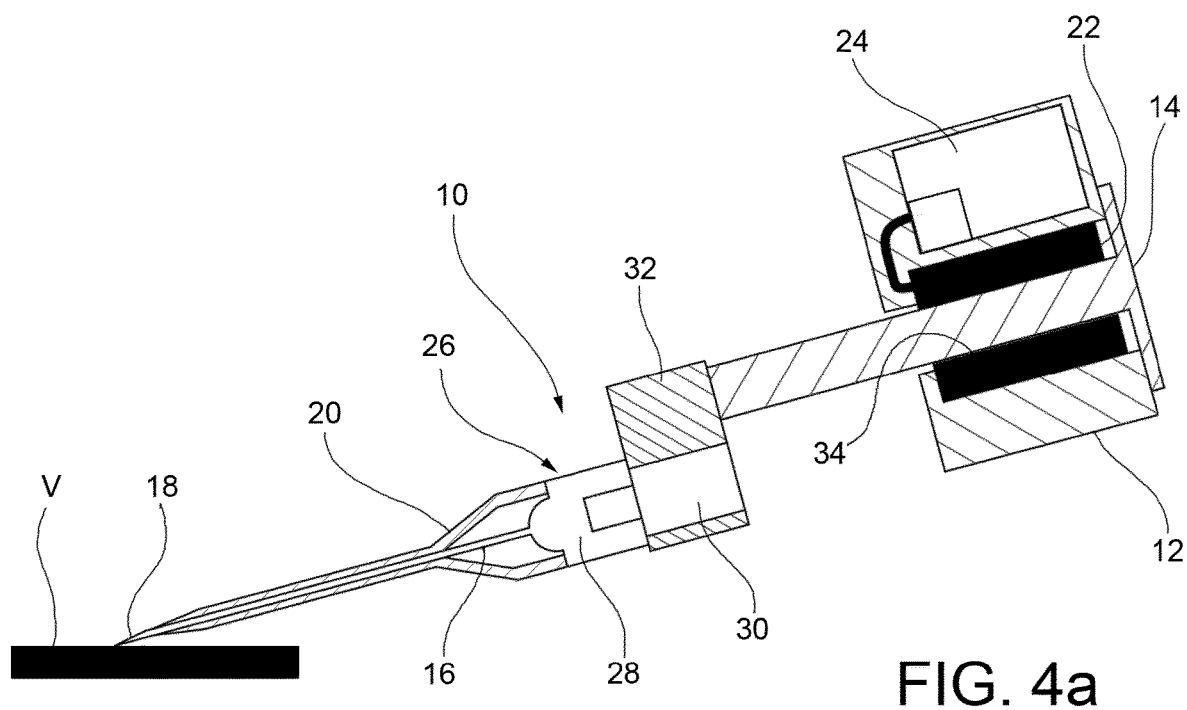
FIGS. 4a and 4b are schematic views showing a third embodiment of a device according to the invention, in the above-mentioned first and second operating conditions, respectively.
Figure 4B:
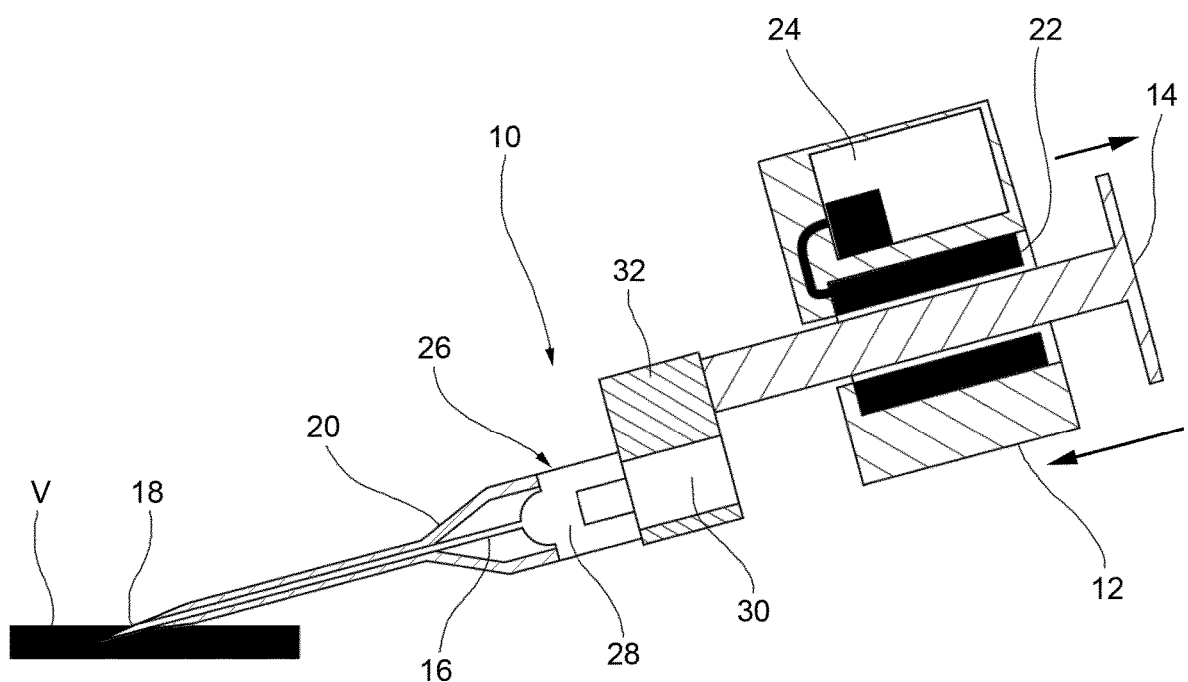

With reference now to FIGS. 4a and 4b, where parts and elements identical or corresponding to those of FIGS. 2a and 2b are designated with the same reference numerals, a third embodiment of the invention is shown therein, which differs from the first embodiment of FIGS. 2a and 2b substantially only in the structure of the decoupling unit 22.

In this third embodiment, in fact, the decoupling unit 22 is formed by a pressurized container of tubular shape which is mounted in the casing 12 so as to move as a single piece with it and defines a central passage 34 through which the shaft 14 extends. When pressurized, the container clamps the shaft 14 inside the passage 34 so that the shaft 14 is fixed to the casing 12 (FIG. 4a). However, when deflated to a low pressure (as a result, for example, of puncturing), the container does not clamp the shaft 14 anymore and the shaft 14 is thus free to move relative to the container, and therefore relative to the casing 12 (FIG. 4b). In this case, the control unit 24 controls the decoupling unit 22 so as to cause deflation of the pressurized container when the control unit 24 determines, based on the signals received from the sensor unit 26, that the needle tip 18 has reached the target position. Accordingly, even though the operator pushes the casing 12 further towards the vein V, or more generally towards the material into which the needle tip 18 has to be inserted, the needle tip 18 is not moved along with the casing 12, but remains in the target position.

Figure 5:
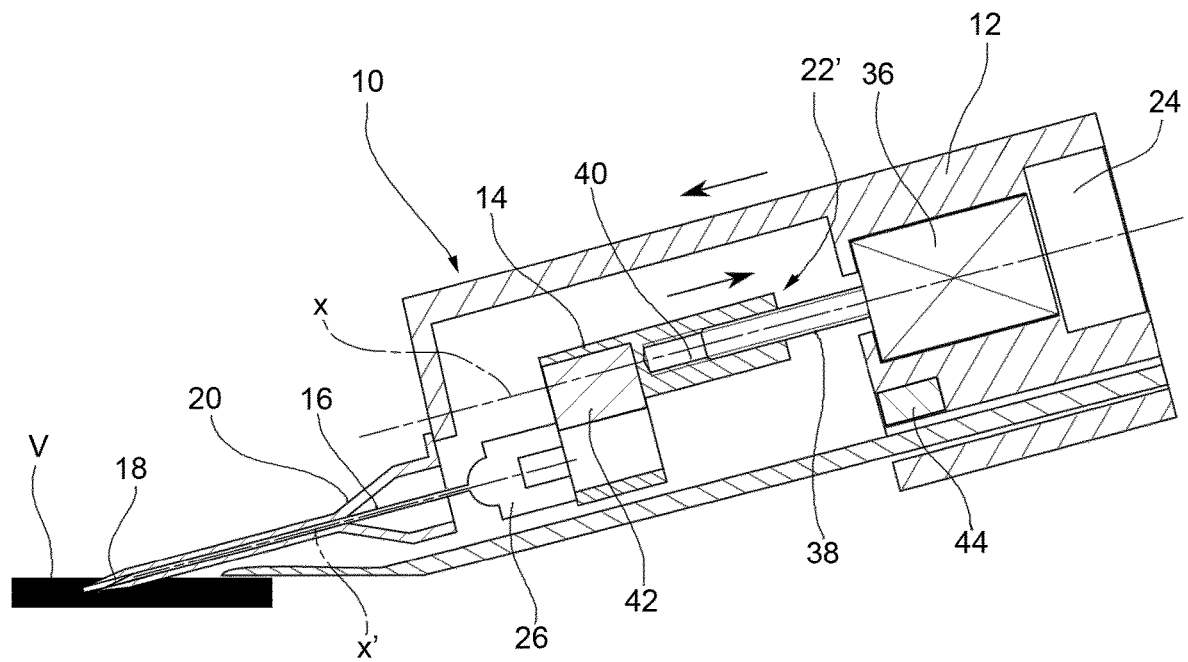
FIG. 5 is a schematic view showing a fourth embodiment of a device according to the invention.

With the reference now to FIG. 5, where parts and elements identical or corresponding to those of the preceding Figures have been given the same reference numerals, according to a further embodiment of the invention the device comprises an actuating unit 22', instead of the decoupling unit 22, which actuating unit 22' is formed by a motorized linear mechanism arranged to move the shaft 14 to and fro along the longitudinal axis x under control of the control unit 24 to keep the needle tip 18 in the target position, for example in a fixed position inside the vein V, automatically compensating for any possible forward or backward motion of the casing 12 produced by the user.

The motorized linear mechanism may comprise an electric motor 36 and a screw and nut mechanism for converting a rotational motion of a screw 38 driven into rotation by the electric motor 36 into a translational motion of a nut 40 along an axis coinciding with, or more generally parallel to, the longitudinal axis x of the shaft 14, the nut 40 being secured to, or alternatively formed in one piece with, the shaft 14. By controlling rotation of the electric motor 36 in one direction or in the opposite direction, the control unit 24 causes the needle 16 to move to and fro relative to the casing 12, in order to automatically insert the needle 16 into the vein V or withdraw the needle 16 from the vein V and/or to actively keep the needle 16 in a fixed position inside the vein V irrespective of any possible movements of the casing 12 produced by the user. In order for the control unit 24 to suitably control the electric motor 36 to keep the needle 16 in a fixed position compensating for any possible movements of the casing 12 produced by the user, the device 10 further includes an axial force sensor 42 or a position sensor 44 to sense the force applied by the user on the casing 12 once the needle tip 18 has reached its target position in the vein V.

According to the illustrated embodiment, the device 10 is also able to withdraw the needle 16 from the vein V while inserting the catheter 20 into the vein V. In this case, the motorized linear mechanism is activated by the control unit 24 to withdraw the shaft 14, and hence also the needle 16, at a higher rate compared to the forward movement of the casing 12 produced by the user, so that the needle 16 is drawn back from the vein V, once the needle tip 18 has punctured the vein, while at the same time the catheter 20 is pushed forward by the casing 12 and thus enters the vein V.

Further embodiments of the device according to the invention, comprising an actuating unit arranged to actively move the shaft, and hence the needle, to and fro relative to the casing to compensate for any possible movements of the latter, and wherein the catheter may be inserted into the vein while at the same time the needle is withdrawn from the vein, are illustrated in FIGS. 6a to 6c, 7a to 7c and 8a to 8c, where parts and elements identical or corresponding to those of FIG. 5 have been given the same reference numerals.

Figure 6A:
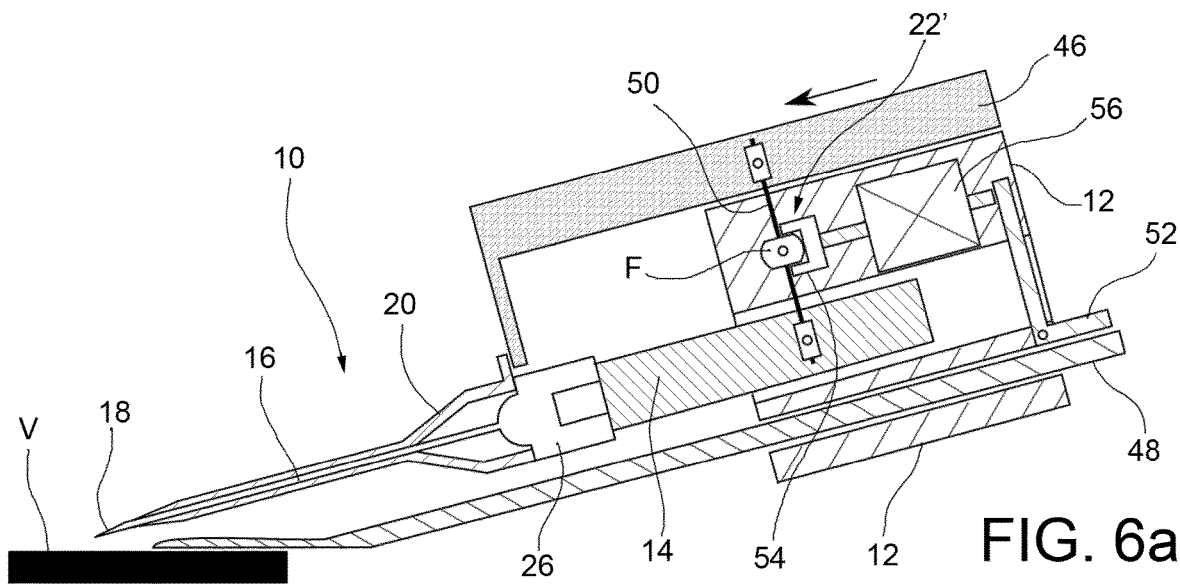
FIGS. 6a, 6b and 6c are schematic views showing a fifth embodiment of a device according to the invention, in a first operating condition where the needle and the catheter are both coupled to the handle and the casing is freely movable relative to the support member along the longitudinal axis of the needle, in a second operating condition where the needle tip has reached a blood vessel and the main body is locked to the support member and in a third operating condition where, with the main body still locked to the support member, the handle is advanced to move the catheter further into the vessel and at the same time the needle is retracted, respectively.
Figure 6B:
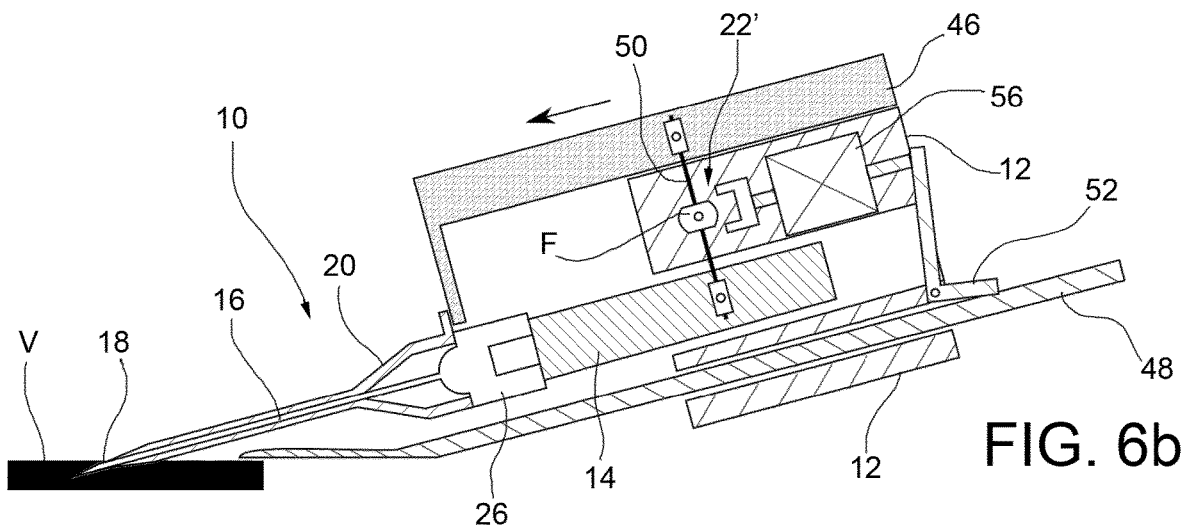
Figure 6C:
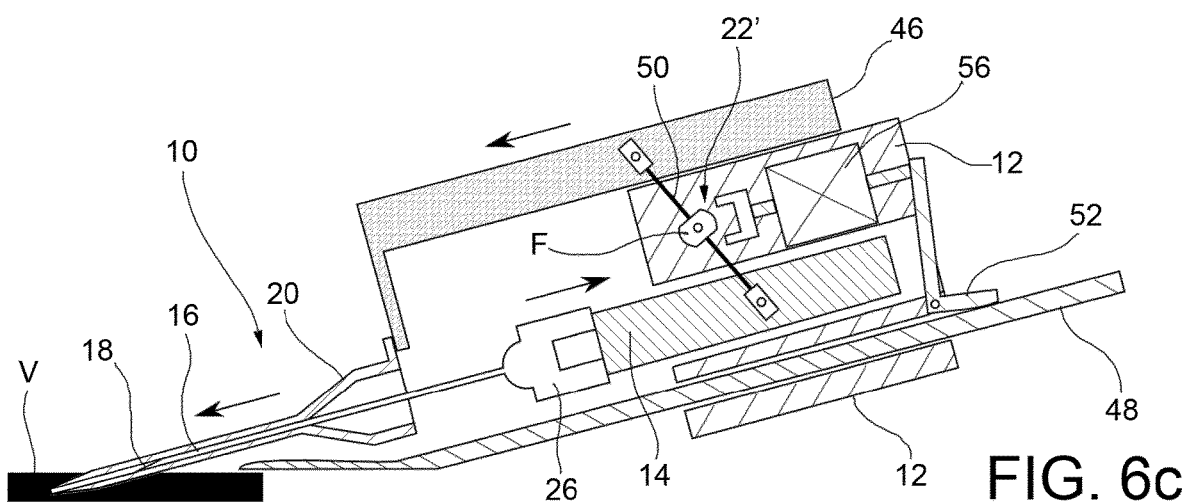

With reference first to the embodiment shown in FIGS. 6a to 6c, the device 10 further comprises a handle 46 operable by the user (or, alternatively, by a linear actuator, for example an electromechanical linear actuator) and a support member 48 that are both slidably mounted on the casing 12 for sliding relative to the latter in a direction parallel to the longitudinal axes x and x'. The handle 46 is connected to the shaft 14 by a swing arm 50 which is hinged at its centre to the casing 12 at a fulcrum F and is hinged at its opposite ends to the handle 46 and to the shaft 14, so that a longitudinal movement of the handle 46 in one direction relative to the casing 12 causes a longitudinally movement of the shaft 14 in the opposite direction relative to the casing 12. The support member 48 may be coupled to the casing 12 by a clutch lever 52 hingedly mounted on the casing 12. The support member 48 is intended to be brought in contact with the material (for example the patient's skin) into which the needle tip 18 has to be inserted, in order to facilitate support of the device 10 during insertion of the needle 16 into the material.

A fork-like locking member 54 operated by a solenoid 56 is operatively associated to the swing arm 50 to lock the latter and prevent it from rotating about its fulcrum F, as shown in FIG. 5a. The solenoid 56 is also configured to control movement of the clutch lever 52 between a first operating position (FIG. 6a), in which the clutch lever 52 does not engage the support member 48 and therefore does not prevent the latter from sliding relative to the casing 12, and a second operating position (FIGS. 6b and 6c), in which the clutch lever 52 engages the support member 48 to couple the latter to the casing 12.

When the solenoid 56 is deactivated, it keeps the locking member 54 in a locking position in which the locking member 54 locks the swing arm 50. At the same time, the clutch lever 52 is in the above-mentioned first operating condition. On the other hand, when the solenoid 56 is activated, it moves the clutch lever 52 in the above-mentioned second operating position and at the same time moves the locking member 54 away from the locking position to allow rotation of the swing arm 50 about its fulcrum F.

When the solenoid 56 is deactivated (see FIG. 6a), and hence when the swing arm 50 is locked by the locking member 54 and the clutch lever 52 is in the above-mentioned first operating position, the operator acting on the handle 46 may move the needle 16 and the catheter 20 towards the vein V while the support member 48 is in contact with the patient's skin, as the clutch lever 52 allows movement of the casing 12, and hence of the shaft 14, relative to the support member 48.

Upon detection by the sensor unit 26 that the needle tip 18 has reached the vein V, the control unit 24 activates the solenoid 56, so that the swing arm 50 is no more locked by the locking member 54 and can therefore rotate around its fulcrum F, while the clutch lever 52 is moved to the second operating position to couple the support member 48 the casing 12 (FIG. 6b). Accordingly, the needle 16 is prevented from advancing further into the vein V.

At this point, as shown in FIG. 6c, further forward movement of the handle 46 by the operator (or, alternatively, by electrical power from an embedded battery pack or from external connection) causes on the one hand a corresponding forward movement of the catheter 20 into the vein V and on the other a pivoting motion of the swing arm 50 about the fulcrum F, an therefore withdrawal of the needle 16 from the vein V.

The device of FIGS. 6a to 6c thus allows to perform the following three distinct actions:
  i) decoupling of the needle 16 from the casing 12 to avoid target overshooting;
  ii) withdrawal of the needle 16; and
  iii) insertion of the catheter 20, this action being performed at the same time as action ii).

The device 10 may be provided with optional LED outputs (not shown) to show that the needle tip 18 has reached the target position, as detected by the sensor unit 26. LED outputs may also provide indications relating to any one of the following states of the device:
a) device 10 ready/not ready;
b) needle 16 coupled to/decoupled from the casing 12;
c) catheter 20 locked/released; and
d) battery level.

The device may also be connected to an external computer system (not shown), either wireless or wired, for real-time transmission of the measurements taken by the sensor unit and/or of internal parameters representing the operating state of the device and for remote control operation.

Figure 7A:
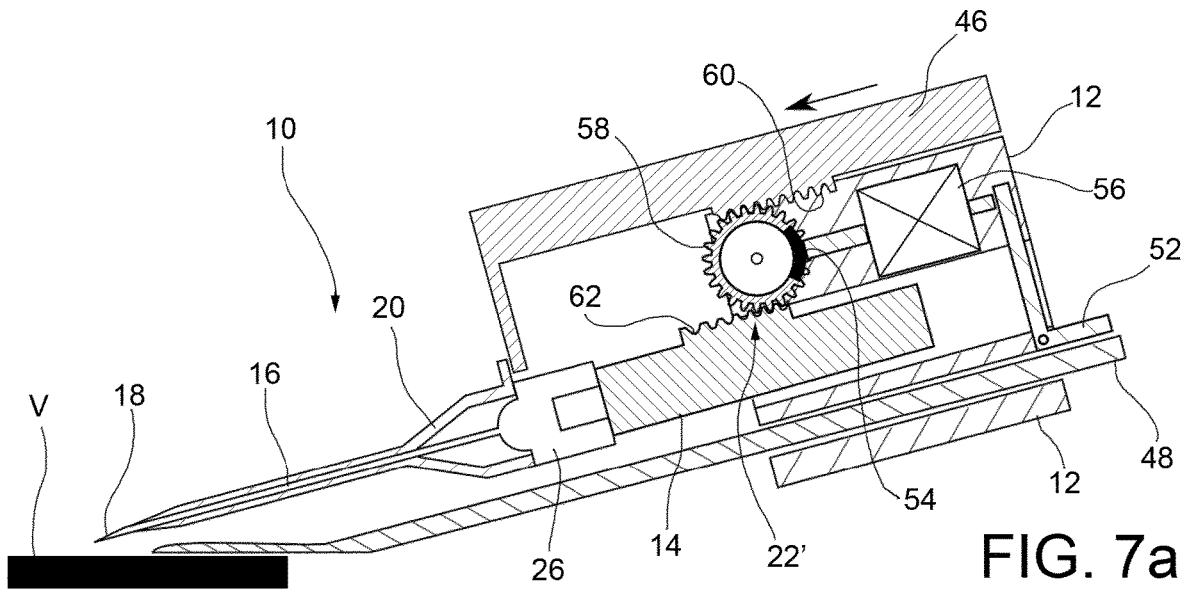
FIGS. 7a, 7b and 7c are schematic views showing a sixth embodiment of a device according to the invention, in said first, second and third operating conditions, respectively.
Figure 7B:
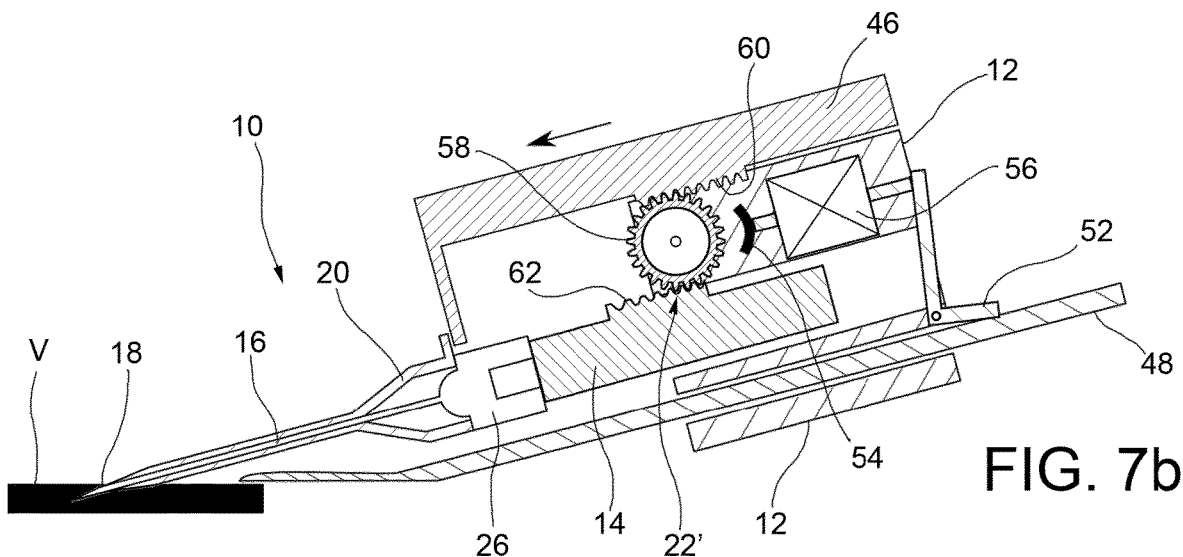
Figure 7C:
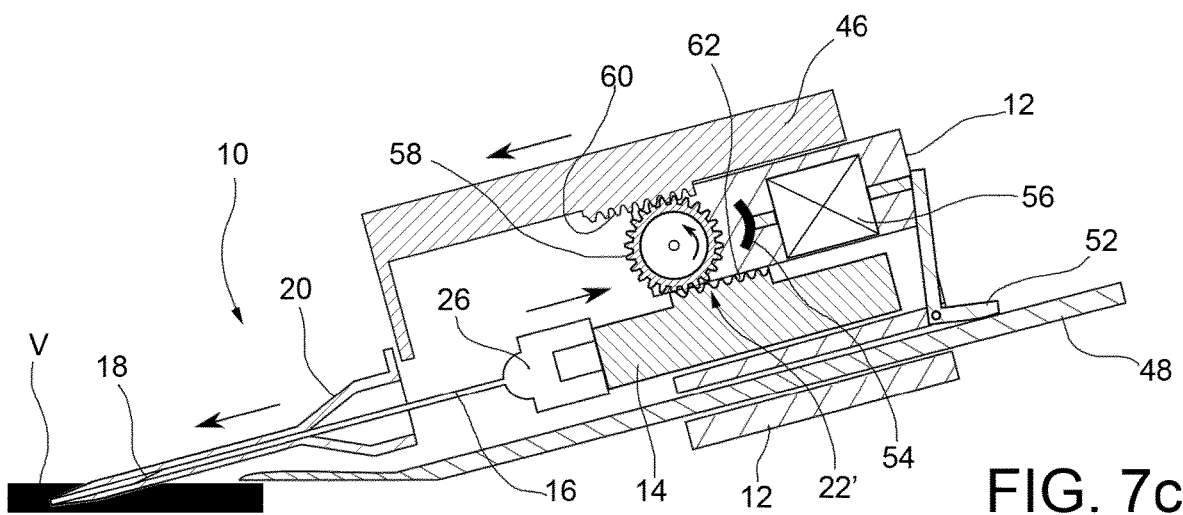

The embodiment of FIGS. 7a to 7c differs from the embodiment of FIGS. 6a to 6c mainly in that the swing arm as a means for converting the translational motion of the handle 46 in one direction into the translational motion of the shaft 14 in the opposite direction is replaced by a gear mechanism comprising a gear wheel 58, which is idly rotatably supported by the casing 12 and meshes both with a first rack 60 of the handle 46 and with a second rack 62 of the shaft 14, and in that the locking member 54 is made as a braking pad arranged to lock the gear wheel 58 by applying on the latter a friction torque.

Also in this embodiment the clutch lever 52 and the locking member 54 are controlled by the solenoid 56 in such a manner that when the solenoid 56 is deactivated (FIG. 7a) the clutch lever 52 does not engage the support member 48 and the locking member 54 locks the gear wheel 58, whereas when the solenoid 56 is activated (FIGS. 7b and 7c) the clutch lever 52 engages the support member 48 and the locking member 54 unlocks the gear wheel 58.

Figure 8A:
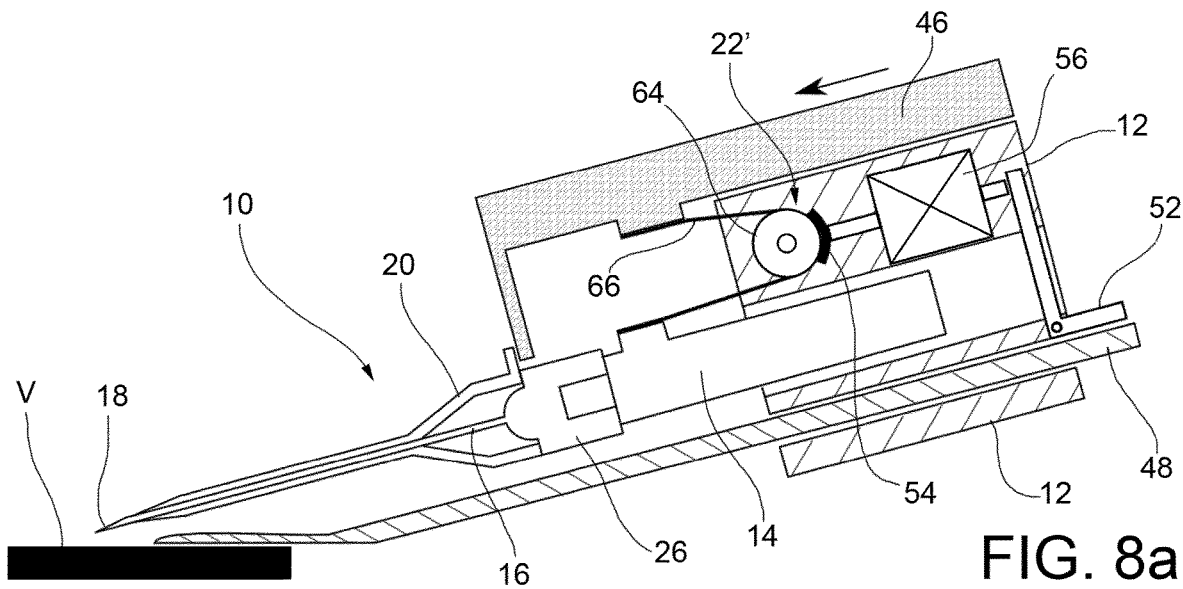
FIGS. 8a, 8b and 8c are schematic views showing a seventh embodiment of a device according to the invention, in said first, second and third operating conditions, respectively.
Figure 8B:
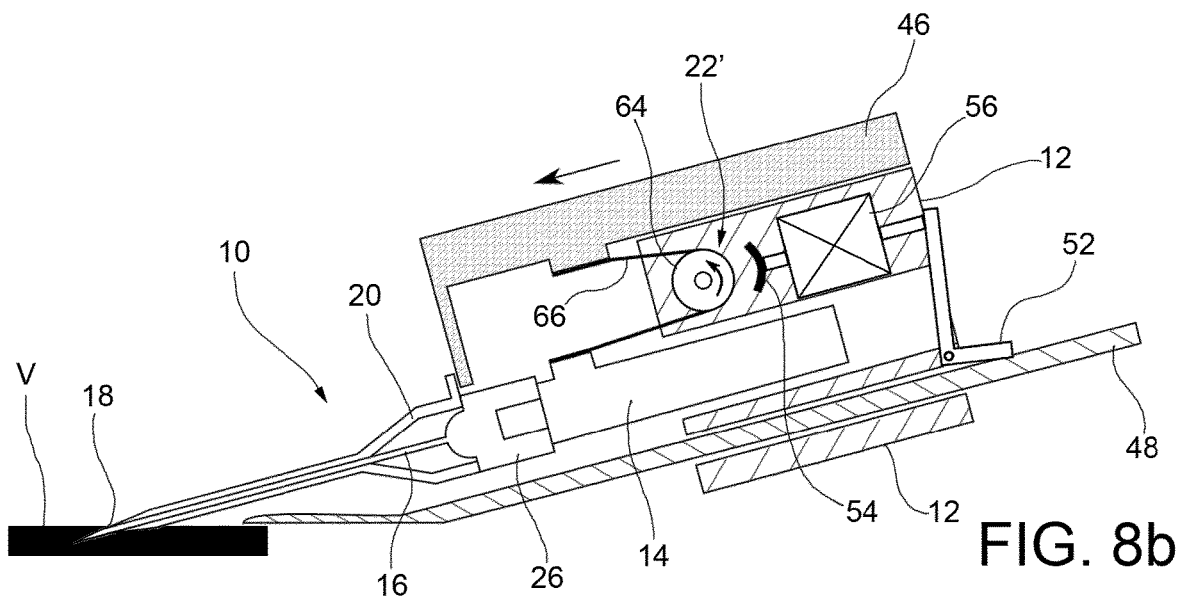
Figure 8C:
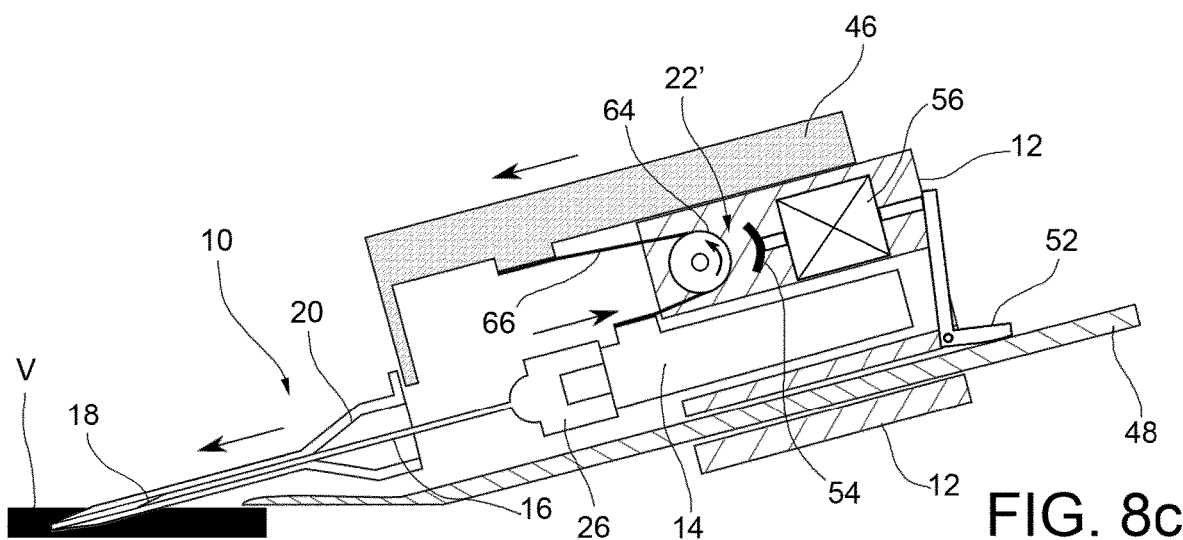

Finally, FIGS. 8a to 8c show a further embodiment that differs from the embodiment of FIGS. 7a to 7c only in that the gear mechanism as a means for converting the translational motion of the handle 46 in one direction into the translational motion of the shaft 14 in the opposite direction is replaced by a belt mechanism comprising a wheel 64 and a belt 66 which is attached at a first end thereof to the handle 46, passes around the wheel 64 and is attached at the opposite end to the shaft 14. Also in this case the wheel 64 may be locked by a locking member 54 made as a braking pad.

As far as the sensor unit 26 is concerned, the description provided above with reference to the embodiments of FIGS. 2a and 2b and FIG. 3 applies also to the other embodiments of the invention shown in FIGS. 4a to 8c.

In view of the above description, the advantages of the invention over the prior art are evident.

First of all, by virtue of its sensor unit, that allows to determine whether the needle tip has reached the target position, and of the decoupling or actuating unit, that allows to decouple the needle from the casing of the device and hence to avoid target overshooting, even though the operator moves the device further towards the material, or to actively move the needle to and fro relative to the casing, the device of the invention allows operators, even those not very skilled, to precisely position the needle tip in the desired position and to keep the needle tip in this position, thereby significantly lowering work stress of the operators, in particular when difficult patients (children, elderly people or diabetic patients) have to be treated.

Furthermore, the device of the invention has a lightweight and compact structure that facilitates handling of the device by the operator and is also not expensive to manufacture.

The principle of the invention remaining unchanged, the embodiments and the constructional details may be greatly modified with respect to those described by way of non-limiting examples, without thereby departing from the scope of the invention as described and claimed herein.

What is claimed is:

1. A hand-held device for inserting a needle into a non-homogeneous material, including a blood vessel, the hand-held device comprising:
a casing configured to be hand-held by an operator;
a shaft extending along a longitudinal axis and carrying at a distal end thereof the needle, the shaft being fitted in the casing and being coupled to the casing to move as a single piece therewith along the longitudinal axis;
a decoupling unit for decoupling the shaft from the casing so that the shaft is movable relative to the casing along the longitudinal axis, wherein said decoupling unit is configured to selectively clamp the shaft to couple the shaft to the casing or unclamp the shaft to allow the shaft to move relative to the casing along the longitudinal axis;
a sensor unit arranged to provide signals indicative of at least one physical characteristic of the non-homogeneous material wherein a needle tip has to be inserted; and
a control unit operatively connected to said decoupling unit and said sensor unit and configured to:
determine, based on the signals received from said sensor unit, whether the needle tip has reached a target position; and
when the needle tip has reached the target position, operate said decoupling unit to decouple the shaft and the needle from the casing to allow the shaft to move in an opposite direction along the longitudinal axis relative to further movement of the casing, to maintain the needle tip in the target position.

2. The hand-held device of claim 1, wherein said decoupling unit comprises an electrical clutch operable between an engaged position, in which said electrical clutch clamps the shaft, so that the shaft is coupled to the casing, and a non-engaged position, in which said electrical clutch unclamps the shaft, thereby allowing the shaft to move relative to the casing.

3. The hand-held device of claim 1, wherein said decoupling unit comprises a pressurized container of tubular shape mounted in the casing so as to move as a single piece with the casing and defining a central passage through which the shaft extends, whereby said container, when pressurized, clamps the shaft inside the passage and, when deflated, does not clamp the shaft thereby allowing the shaft to move relative to the container.

4. The hand-held device of claim 1, wherein said sensor unit is configured to sense an acoustic or near-acoustic signal of the needle or an electrical impedance between the needle tip and the shaft.

5. A hand-held device for inserting a needle into a non-homogeneous material, including a blood vessel, the hand-held device comprising:
a casing configured to be hand-held by an operator;
a shaft extending along a longitudinal axis and carrying at a distal end thereof the needle, the shaft being fitted in the casing and being coupled to the casing to move as a single piece therewith along the longitudinal axis;
an actuating unit for actively moving the shaft relative to the casing in either direction along the longitudinal axis;

a sensor unit arranged to provide signals indicative of at least one physical characteristic of the non-homogeneous material wherein a needle tip has to be inserted; and a control unit operatively connected to said actuating unit and said sensor unit and configured to:
  determine, based on the signals received from said sensor unit, whether the needle tip has reached a target position; and
  when the needle tip has reached the target position, operate said actuating unit to move the shaft and the needle in an opposite direction relative to further movement of the casing to maintain the needle tip in the target position.

6. The hand-held device of claim 5, wherein said actuating unit comprises a motorized linear mechanism configured to move the shaft to and fro along the longitudinal axis under control of said control unit to keep the needle tip in the target position, automatically compensating for any forward or backward motion of the casing produced by the operator relative to said non-homogeneous material.

7. The hand-held device of claim 6, wherein said motorized linear mechanism includes an electric motor and a motion conversion mechanism arranged to convert a rotary motion produced by the electric motor into a translational motion of the shaft along the longitudinal axis.

8. The hand-held device of claim 5, further comprising a catheter mounted around the needle and an operating handle movable relative to the casing in a direction parallel to the longitudinal axis to cause insertion of the catheter into said non-homogeneous material.

9. The hand-held device of claim 8, wherein said actuating unit is arranged to cause the shaft to move relative to the casing, when the needle tip has reached said target position and the operating handle is moved relative to the casing to insert the catheter into said non-homogeneous material, in a direction opposite to a direction of movement of the operating handle to withdraw the needle from said non-homogeneous material.

10. The hand-held device of claim 8, further comprising a support member configured to support the hand-held device on said non-homogeneous material and slidably mounted relative to the casing in the direction parallel to the longitudinal axis, and a clutch member switchable between a first position, wherein said clutch member allows the casing to slide freely relative to the support member, and a second position, wherein said clutch member couples the casing to the support member preventing relative movement of the casing with respect to the support member.

* * * * *